United States Patent [19]
Kabadi et al.

[11] Patent Number: 5,356,896
[45] Date of Patent: Oct. 18, 1994

[54] STABILIZED PHARMACEUTICAL COMPOSITIONS COMPRISING AN HMG-COA REDUCTASE INHIBITOR COMPOUND

[75] Inventors: Mohan B. Kabadi, Marlboro; Richard V. Vivilecchia, Rockaway, both of N.J.

[73] Assignee: Sandoz Ltd., Basel, Switzerland

[21] Appl. No.: 995,252

[22] Filed: Dec. 22, 1992

Related U.S. Application Data

[63] Continuation-in-part of Ser. No. 805,667, Dec. 12, 1991, abandoned.

[51] Int. Cl.$^5$ .............. A61K 31/505; A61K 31/435; A61K 31/44; A61K 31/405; A61K 31/19
[52] U.S. Cl. .................... 514/256; 514/277; 514/306; 514/415; 514/569; 514/970
[58] Field of Search .............. 514/415, 970, 256, 277, 514/306, 569

[56] References Cited

U.S. PATENT DOCUMENTS

| | | | |
|---|---|---|---|
| 3,865,935 | 2/1975 | Amann | 424/181 |
| 3,891,755 | 6/1975 | Mehta | 424/157 |
| 3,952,096 | 4/1976 | Godfrey | 424/156 |
| 4,342,767 | 8/1982 | Albers-Schonberg et al. | 424/250 |
| 4,744,987 | 5/1988 | Mehra et al. | 424/156 |
| 4,755,385 | 7/1988 | Etienne et al. | 424/154 |
| 4,786,505 | 11/1988 | Lovgren et al. | 424/468 |
| 4,853,230 | 8/1989 | Lovgren et al. | 424/466 |
| 4,929,605 | 5/1990 | Domet et al. | 514/54 |
| 5,004,651 | 4/1991 | Becker | 424/465 |
| 5,030,447 | 7/1991 | Joshi et al. | 424/80 |
| 5,045,321 | 9/1991 | Makino et al. | 424/475 |

FOREIGN PATENT DOCUMENTS

| | | | |
|---|---|---|---|
| 114027 | 7/1984 | European Pat. Off. | 209/18 |
| 375156 | 6/1990 | European Pat. Off. | |
| 401705 | 12/1990 | European Pat. Off. | |

OTHER PUBLICATIONS

CA 114 (6) 49589k, Dennick, 1990.

*Primary Examiner*—Marianne M. Cintins
*Assistant Examiner*—Kimberly R. Jordan
*Attorney, Agent, or Firm*—Robert S. Honor; Richard E. Vila; Diane E. Furman

[57] ABSTRACT

A pharmaceutical dosage form comprising an HMG-CoA reductase inhibitor compound, e.g., fluvastatin sodium, is disclosed which is stabilized against pH-related degradation by an alkaline stabilizing medium capable of imparting a pH of at least 8 to an aqueous solution or dispersion of the composition.

27 Claims, No Drawings

STABILIZED PHARMACEUTICAL COMPOSITIONS COMPRISING AN HMG-COA REDUCTASE INHIBITOR COMPOUND

This application is a continuation-in-part of application Ser. No. 07/805,667 filed Dec. 12, 1991 and now abandoned.

The present invention relates to a pharmaceutical composition comprising a pH sensitive medicament, which has enhanced storage stability.

Certain HMG-CoA reductase compounds, i.e. cholesterol biosynthesis inhibitors, useful in the treatment of hyperlipoproteinemia and atherosclerosis, which are compounds of the formula

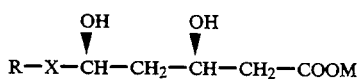

wherein
R is an organic radical,
X is —CH₂—CH₂— or —CH=CH—, preferably (E)—CH=CH—, and
M is a physiologically acceptable cation, such as an alkali metal cation or ammonium, preferably sodium or potassium, and especially sodium,
are extremely susceptible to degradation at pH below about 8. An example of such a compound comprises the compound having the USAN designation fluvastatin sodium (hereinafter "fluvastatin"), of the formula:

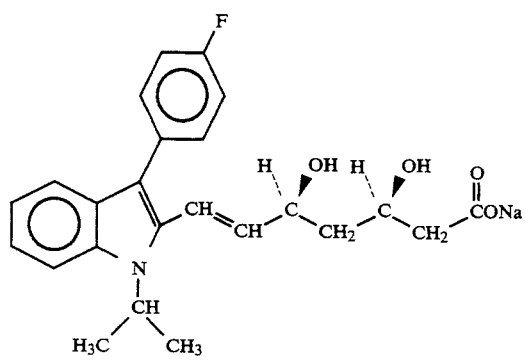

[i.e. erythro-R*, S*-(E)-(±)-7-[3-(4-fluorophenyl)-1-(1-methylethyl)-1H-indol-2-yl]-3,5-dihydroxy-6-heptenoic acid, sodium salt]. The above-indicated erythro racemate may be resolved into two optically pure enantiomers, the 3R,5S and 3S,5R isomers, of which the former is preferred [see European Patent Application EP-A-114,027].

For example, we have found that the degradation kinetics of fluvastatin in aqueous solution at various pH are as illustrated below:

| | % fluvastatin remaining at 37° C. | |
| pH | after 1 hour | after 24 hrs |
| --- | --- | --- |
| 7.8 | 98.3 | 98.0 |
| 6.0 | 99.6 | 97.1 |
| 4.0 | 86.7 | 25.2 |
| 1.0 | 10.9 | 0 |

The above-indicated instability of fluvastatin and related HMG-CoA reductase compounds we believe is due to the extreme lability of the β,δ-hydroxy groups on the heptenoic acid chain and the presence of the double bond, such that at neutral to acidic pH, the compounds readily undergo elimination or isomerization or oxidation reactions to form conjugated unsaturated aromatic compounds, as well as the threo isomer, the corresponding lactones, and other degradation products.

In order to achieve marketable dosage forms comprising such a compound, it is essential to adequately protect it against pH-related destabilization.

Additionally, the heat and light sensitivity as well as hygroscopicity of the subject compounds impose particular requirements in the manufacture and storage of pharmaceutical dosage forms.

We have surprisingly been able to prepare such compositions having extended periods of storage stability, e.g., whereby at least about 95% of the initial amount of the drug is active after 2 years at +25° C. and +30° C. and for longer periods.

Compositions of the invention on oral administration can provide rapid and essentially complete intestinal absorption of drug substance.

It is a further advantage that the stabilized compositions of the invention can be readily prepared by aqueous or other solvent-based techniques, e.g. wet granulation.

In one aspect the present invention provides a pharmaceutical composition comprising an HMG-CoA compound of the formula

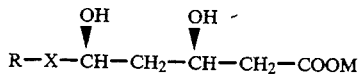

wherein
R is an organic radical, preferably free of acidic groups
X is —CH=CH—, preferably (E)—CH=CH—, and
M is a physiologically acceptable cation,
and an alkaline stabilizing medium capable of imparting a pH of at least 8 to an aqueous solution or dispersion of the composition.

The compositions comprise the drug substance and an "alkaline stabilizing medium," said alkaline medium being capable of stabilizing the composition by imparting a pH of at least 8 to an aqueous solution or dispersion of the composition. Preferably the compounds of formula I and the alkaline medium are in intimate contacting association in the composition to achieve optimal stability of the medicament.

The resulting composition has been found to provide an extended storage life of the compounds of formula I, even in the presence of moisture or when such compositions additionally comprise otherwise potentially reactive excipients, such as lactose. The stability of the drug substance in compositions of the invention can be at least 95%, and is typically between 98% and 99%, after 18 months at 25° C., and for even longer periods.

The terms "alkaline stabilizing medium," "alkaline medium" or "base" employed herein shall refer to one or more pharmaceutically acceptable substances capable of imparting a pH of at least 8, and preferably at least 9, and up to about pH 10, to an aqueous solution or dispersion of the composition of the invention. More particularly, the alkaline stabilizing medium creates a "micro-pH" of at least 8 around the particles of the composition when water is adsorbed thereon or when water is added in small amounts to the composition. The alkaline medium should otherwise be inert to the compounds of formula I. The pH may be determined by taking a unit dosage of the composition containing e.g. 20 mg of fluvastatin or the equivalent amount of another compound falling under formula I and dispersing or dissolving the composition in 10 to 100 ml of water.

The pharmaceutically acceptable alkaline substance(s) which comprise the alkaline medium may range from water-soluble to sparingly soluble to essentially water-insoluble.

Examples of water-soluble alkaline substances capable of imparting the requisite basicity include certain pharmaceutically acceptable inorganic carbonate salts such as sodium or potassium carbonate, sodium bicarbonate, or potassium hydrogen carbonate; phosphate salts selected from, e.g., anhydrous sodium, potassium or calcium dibasic phosphate, or trisodium phosphate; as well as alkali metal hydroxides such as sodium, potassium, or lithium hydroxide; and mixtures of the foregoing.

An example of a stabilized composition according to the invention may comprise: 0.5 to 60 wt. % (weight %), typically 0.5 to 40 wt. %, drug substance (e.g., fluvastatin); and 0.1 to 35 wt. %, preferably 1–15 wt. %, of soluble carbonate compound, for example, selected from sodium bicarbonate, sodium carbonate and mixtures thereof.

Examples of water-insoluble or sparingly soluble alkaline substances also potentially useful to comprise the stabilizing alkaline medium in the compositions comprise compounds commonly employed in antacid formulations (e.g., magnesium oxide, hydroxide or carbonate; magnesium hydrogen carbonate; aluminum or calcium hydroxide or carbonate; composite aluminum-magnesium compounds, such as magnesium aluminum hydroxide): as well as pharmaceutically acceptable salts of phosphoric acid such as tribasic calcium phosphate; and mixtures thereof.

Of the above-mentioned alkaline substances, the "pharmaceutically acceptable carbonate salts," by which is meant pharmaceutically acceptable inorganic carbonate and bicarbonate salts, e.g., sodium carbonate, sodium bicarbonate, calcium carbonate, and mixtures thereof, have been found particularly effective to comprise the alkaline medium.

Compositions also having particularly attractive storage stability comprise, as an alkaline medium, both a water-soluble alkaline excipient and a water-insoluble or sparingly soluble alkaline excipient.

For example, substantial improvements in stability and other advantages have been achieved by employing an alkaline medium comprising a water-soluble carbonate salt and a water-insoluble carbonate salt, especially, the combination of sodium bicarbonate (or carbonate) with calcium carbonate.

Sodium bicarbonate advantageously serves to neutralize acidic groups in the composition in the presence of moisture which may adsorb onto particles of the composition during storage. The calcium carbonate exerts a buffering action in the stored composition, without apparent effect on drug release upon ingestion. It has further been found that the carbonate salts sufficiently stabilize the drug substance such that conventional water-based preparative techniques, e.g. trituration with water or wet granulation, can be utilized to prepare stabilized compositions of the invention.

The calcium carbonate can be a precipitated or ground material, but is preferably precipitated.

The alkaline medium will be present in the compositions in an amount sufficient to impart a pH of e.g. at least 8, and preferably at least 9, and as high as pH 10, to an aqueous solution or dispersion of the composition. In general, the compositions of the invention comprise from about 0.1 to 60 wt. % (typically, 0.5 to 40 wt. %) drug substance; and from about 0.1 to 60 wt. %, preferably 20 to 35 wt. %, alkaline medium.

The amount of a particular stabilizing excipient to be employed will depend to some extent on the intended manufacturing process. In compositions to be tableted, for example, calcium carbonate should not exceed an amount which can be conveniently subjected to compression, and will generally be used in combination with a more readily compressible alkaline substance, e.g., sodium bicarbonate. On the other hand, capsule dosage forms may comprise higher levels of poorly compressible excipients, provided that the overall composition remains sufficiently free-flowing and processible.

A solid unit dosage composition may have the ratio of water soluble carbonate to insoluble carbonate from e.g. 1:40 to 2:1.

An exemplary tablet of the invention may comprise about 2:1 to 1:2 by weight calcium carbonate to sodium bicarbonate. A capsule composition may comprise these excipients in a ratio of, for example, 25:1 to 35:1 by weight.

In addition to the drug substance and alkaline medium, a filler is also generally employed in the compositions to impart processability. Potentially suitable filler materials are well-known to the art (see, e.g., Remington's *Pharmaceutical Sciences*, 18th Ed. (1990), Mack Publishing Co., Easton, Pa., pp. 1635–1636), and include lactose and other carbohydrates, pregelatinized starch, e.g., starch 1500 ® (Colorcon Corp.), corn starch, dicalcium phosphate, cellulose, microcrystalline cellulose, sugars, sodium chloride, and mixtures thereof, of which lactose, microcrystalline cellulose, pregelatinized starch, and mixtures thereof, are preferred.

Owing to its superior disintegration and compression properties, microcrystalline cellulose (Avicel ®, FMC Corp.), and mixtures comprising microcrystalline cellulose and one or more additional fillers, e.g., pregelatinized starch, are particularly useful.

The total filler is present in the compositions in an amount of about 1 to 65 wt. %, based on the total composition.

Other ingredients which may be incorporated into the compositions to facilitate processing and/or provide enhanced properties of the product dosage form, include well-known tableting binders (e.g., gelatin, sugars, natural and synthetic gums, such as carboxymethylcellulose, methylcellulose, polyvinylpyrrolidone, hydroxypropylmethylcellulose), microcrystalline cellulose, and mixtures of the foregoing; disintegrants (e.g., cross-linked carboxymethylcellulose, croscarmelose, crospovidone, sodium starch glycolate), lubricants (e.g., magnesium stearate, hydrogenated vegetable oil, carnauba wax and the like); flow agents (e.g., silicon dioxide), anti-adherents or glidants (e.g., talc) as well as sweeteners, coloring mediums (e.g., iron oxide, aluminum lakes), flavoring mediums, antioxidants, etc. Selection of a particular ingredient or ingredients and the amounts used will be readily determinable by one skilled in the art by reference to standard procedures and practices for preparing tableted or encapsulated or other dosage forms. In general, an effective amount of a tableting binder will comprise about 1 to 10 wt. %, and preferably 1 to 5 wt. %; anti-adherents or gildants, about 1 to 10 wt. %; disintegrants, about 1 to 5 wt. %, and lubricants, about 0.1 to 2 wt. %, based on the total composition.

Such compositions may be formulated by known means to provide standard unitary oral dosages of compound, e.g., 5 mg, 10 mg, 20 mg, 40 mg, etc., in the form of capsules, tablets, pellets, etc.

Enteric film coating materials may optionally be applied to oral tablets, pellets or capsules to protect against premature degradation of the drug substance by gastric acid prior to reaching the intestinal absorption site. Examples of such materials are well-known and include hydroxypropylmethylcellulose phthalate, cellulose acetate phthalate, polyvinyl acetate phthalate, methylcellulose phthalate, copolymerized methacrylic acid/methacrylic acid methyl esters (e.g., Eudragit ®, Rohm Pharma). The enteric coating is preferably applied to result in about a 5 to 12, preferably 8 to 10, weight percent increase of the capsule, pellet or tablet core.

Tableted compositions of the invention are desirably coated to protect against moisture and light discoloration, and to mask the bitter taste of the drug. Either the enteric coating may contain opacifiers and colorants, or a conventional opaque film coating may be applied to the tablet core, optionally after it has been coated with an enteric substance.

Examples of suitable film formers in film coating formulations to be applied to compositions of the invention comprise, e.g., polyethylene glycol, polyvinylpyrrolidone, polyvinyl alcohol, hydrophilic polymers such as hydroxypropylcellulose, hydroxymethylcellulose, and hydroxypropylmethylcellulose or the like, of which hydroxypropylmethylcellulose (e.g., Opadry Yellow$^T$, Colorcon Corp.) is preferred. Hydrophobic film-formers which may be applied using an organic solvent vehicle comprise, for example, ethyl cellulose, cellulose acetate, polyvinyl alcohol-maleic anhydride copolymers, etc.

The film coating may be generally applied to achieve a weight increase of the pellet or core or tablet of about 1 to 10 wt. %, and preferably about 2 to 6 wt. %.

Other conventional enteric or film coating formulation ingredients include plasticizers, e.g., polyethylene glycol (e.g. polyethylene glycol 6000), triethylcitrate, diethyl phthalate, propylene glycol, glycerin, butyl phthalate, in conventional amounts, as well as the above-mentioned opacifiers such as titanium dioxide, and colorants, e.g. iron oxide, aluminum lakes, etc.

The enteric or film coatings can be applied by conventional techniques in a suitable coating pan or fluidized bed apparatus using water and/or conventional organic solvents (e.g., methyl alcohol, ethyl alcohol, isopropyl alcohol), ketones (acetone, ethylmethyl ketone), chlorinated hydrocarbons (methylene chloride, dichloroethane), etc.

A composition according to the invention comprises the following (in weight percent based on the total composition):

0.1 to 60 wt. % (typically 0.5 to 40 wt. %) compound (e.g., fluvastatin), 0.1 to 60 wt. % alkaline stabilizing medium (e.g., carbonate salts), and 1 to 65 wt. % filler (e.g., microcrystalline cellulose).

An example of such a composition comprises (in weight percent based on the total composition): 0.5 to 60 wt. % HMG-CoA reductase compound (e.g., fluvastatin), 10 to 55 wt. % (e.g., 10 to 35 wt. %) alkaline medium (e.g., carbonate salts), and 10 to 65 wt. % (e.g., 20 to 65 wt. %) filler (e.g., microcrystalline cellulose).

Another example of a composition according to the invention comprises (in weight percent based on the total composition):

0.5 to 60 wt. %, drug compound (e.g., fluvastatin), 5 to 40 wt. % (e.g., 10 to 40 wt. %) calcium carbonate, 0.5 to 20 wt. % (e.g., 0.5 to 15 wt. %) sodium bicarbonate, and 10 to 65 wt. % filler (e.g., microcrystalline cellulose).

An example of a capsule composition according to the invention comprises (in weight percent based on the total composition):

0.5 to 60 wt. % (typically 0.5 to 40 wt. %) drug compound (e.g., fluvastatin), 25 to 40 wt. % calcium carbonate, 0.5 to 10 wt. % sodium bicarbonate, and 20 to 35 wt. % microcrystalline cellulose, and optional additional filler (e.g., pregelatinized starch) in an amount of 15 to 30 wt. %.

An example of an tableted composition according to the invention comprises (in weight percent based on the total composition):

0.5 to 60 wt. % drug compound (e.g., fluvastatin), 5 to 20 wt. % calcium carbonate, 5 to 20 wt. % sodium bicarbonate, and 50 to 65 wt. % microcrystalline cellulose.

The stabilized compositions of the invention may be prepared by various techniques and manufacturing processes generally known to the art.

In preparing the compositions it is important that the drug substance and the alkaline medium be brought into intimate contacting association. Dry blending these components to achieve a substantially homogeneous mixture (preferably prior to addition of filler and remaining excipients), followed by a compression step, can achieve the desired intimate contacting.

However, to obtain very stable formulations, an aqueous or other solvent-based preparative process is preferably utilized, whereby the drug substance and alkaline medium are blended together in the presence of minor amounts of, e.g., water, to provide particles containing the drug and alkaline substance in intimate admixture. Given the hygroscopicity and moisture sensitivity of HMG-CoA reductase inhibitor compounds such as fluvastatin, it is unexpected that the drug substance is sufficiently stabilized by the alkaline medium to resist degradation by such techniques.

In one embodiment of such a process, the drug and alkaline medium are triturated with water, and the resulting particles are dried. Filler and remaining excipients, which have been set aside to comprise an "external phase" of said particles, are then blended with the dried particles to result in a composition suitable for encapsulation, tableting or the like.

In another embodiment of a solvent-based process which can assist subsequent drying in a fluidized bed, the drug substance and alkaline medium are wet granulated by known techniques, i.e. blended in the moistened state, together with an amount of the filler material. The thus-formed granules, after drying, are then combined with any remaining filler and other set-asides, e.g., binder, lubricant, and can therefore be tableted, encapsulated, or otherwise shaped into a dosage form.

It is important in order to achieve extended shelf life of the compositions that the particles prepared by trituration or wet granulation or other aqueous-based process be substantially completely dried, i.e. to a weight loss on drying (L.O.D.) of not greater than 3%, and preferably not greater than 2%.

Drying is conventionally performed by tray drying or in a fluidized bed, preferably the latter. Drying is typically performed at about 50° C. inlet temperature, and below 50% RH.

In preparing the compositions, the drug substance and the remaining ingredients of the dosage form (except lubricant) are preferably passed through 30 to 40 mesh screen prior to being triturated or wet granulated, the drug substance generally being screened first and then blended with the screened excipients. Additionally, the dried particles or granules are passed through 18 to 20 mesh screen for proper blending with the set asides.

Compositions to be tableted are typically passed through a smaller screen, e.g., 24 mesh, before being combined with a lubricant and subjected to compression; and this screening step generally requires an additional drying step, whereby the wet particles or granules obtained by trituration or granulation are dried to an L.O.D. of 6–8%, then passed through 12 to 14 mesh screen, and then redryed to an L.O.D. of 2–3%.

In an alternative preparative procedure to the above-described trituration or wet granulation techniques, the drug substance and the alkaline stabilizing medium can be co-lyophilized, i.e. freeze-dried, from aqueous solution, advantageously as a step in situ of the drug manufacturing process.

As exemplified in U.S. Pat. No. 4,739,073, which is incorporated by reference herein, fluvastatin sodium, as well as the sodium salts or other pharmaceutically acceptable salts of other HMG-CoA reductase inhibitor compounds of the invention, is typically prepared by hydrolyzing the corresponding ester compound with, e.g., sodium hydroxide in ethanol solution. The ethanol or other organic phase is then evaporated and water is added to the remaining drug-containing phase to form an aqueous solution from which (generally after extraction with an organic solvent), the HMG-CoA reductase inhibitor compound is recovered by lyophilization.

It has been found that a water-soluble stabilizing alkaline substance such as sodium carbonate or bicarbonate or other alkaline medium, can be added in situ to the above-described aqueous phase comprising the fluvastatin or other HMG-CoA reductase inhibitor compound, and upon subjecting this aqueous phase to a freeze-drying procedure, there can be obtained particles comprising the drug compound co-lyophilized with the added alkaline substance.

Very good contacting of the drug and stabilizer can thereby be achieved, to the extent that stable compositions of the invention may be prepared, for example, from the drug and sodium carbonate in a weight ratio of about 10:1 to 100:1. For example, a co-lyophilized composition of the invention comprising as low as 0.1% by weight sodium carbonate has been found effective to provide a highly stabilized drug composition.

Lyophilization is carried out by conventional procedures and equipment, by first reducing the temperature of the solution from room temperature to below freezing, typically down to in the range of about −45° C., and applying a high vacuum, e.g., in the range of about 3 mm Hg or less, and thereafter raising the temperature to at or above room temperature, to result in vaporization of the aqueous solvent. The recovered particles are essentially free of solvent, and optimally comprise a substantially homogeneous mixture of the drug and stabilizer.

The obtained particles can then be combined with other excipients, e.g., filler, binder, lubricant, etc.

The compositions of the invention, obtained by any of the above techniques, can be formed into a dosage form by techniques and procedures well-known to the art, e.g., tableting, encapsulation, pelleting, molding, etc.

As previously indicated, an enteric and/or film coating composition can be applied to the dosage form for its particular benefits.

Enteric or film coating of a microcrystalline cellulose-based tablet with a water-based film coating formulation is desirably carried out at a bed temperature of 30°–50° C., an inlet temperature of 50°–80° C. and a relative humidity (RH) of less than 50%.

It is important for achieving optimal stability of the formulation that the enteric and/or film coated dosage form be dried to a moisture content which is not greater than 4% and preferably not greater than 3%.

The resulting tableted or capsule dosage forms should be protected during storage against thermal or light induced oxidation as well as moisture contamination.

Capsules and tablets prepared from the compositions of the invention have been found to have an attractive storage stability.

The dosage forms are suitable for the intended use. Film-coated tablets or capsules of the invention have a disintegration time of about 10 to 30 minutes. Enteric coated tablets or capsules have a disintegration time in general of about 30 minutes to about 6 hours.

Dosage regimens for treating hyperlipoproteinemia or atherosclerosis by administering to a patient a compound of formula Ia are set forth in U.S. Pat. No. 4,739,073 at col. 34, 11.20–54, which is incorporated by reference. For example, the oral daily dosage is indicated to be 0.1 to 10 mg./kg. body weight or, for larger primates, 0.1 to 140 mg.

In addition to compositions comprising fluvastatin sodium, the present invention is intended to cover compositions comprising other HMG-CoA reductase inhibitor compounds of formula I herein, including both the erythro racemate and its constituent isomers (i.e. the 3R,5S and 3S,5R isomers, preferably the 3R,5S isomer). Said compounds are disclosed, e.g., in the following commonly assigned patents, published patent applications and publications which are all hereby incorporated herein by reference:

U.S. Pat. No. 4,739,073, and EP-A-114,027 (R=indolyl and derivatives thereof); EP-A-367,895 (R=pyrimidinyl and derivatives thereof); U.S. Pat. No. 5,001,255 (R=indenyl and derivatives thereof); U.S. Pat. No. 4,613,610 (R=pyrazolyl and derivatives thereof); U.S. Pat. No. 4,851,427 (R=pyrrolyl and derivatives thereof); U.S. Pat. Nos. 4,755,606 and 4,808,607 (R=imidazolyl and derivatives thereof); U.S. Pat. No. 4,751,235 (R=indolizinyl and derivatives thereof); U.S. Pat. No. 4,939,159 (R=azaindolyl and derivatives thereof); U.S. Pat. No. 4,822,799 (R=pyrazolopyridinyl and derivatives thereof); U.S. Pat. No. 4,804,679 (R=naphthyl and derivatives thereof); U.S. Pat. No. 4,876,280 (R=cyclohexyl and derivatives thereof); U.S. Pat. No. 4,829,081 (R=thienyl and derivatives thereof); U.S. Pat. No. 4,927,851 (R=furyl and derivatives thereof); U.S. Pat. No. 4,588,715 (R=phenylsilyl and derivatives thereof); and F. G. Kathawala, Medicinal Research Reviews, Vol. 11

(2), p.121–146 (1991), and F. G. Kathawala, Atherosclerosis Research - Review, June 1992, p. B73-B85.

Further compounds of formula I are disclosed e.g. in EP-A-304,063 (R=quinolinyl and derivatives thereof); EP-A-330,057 and U.S. Pat. Nos. 5,026,708 and 4,868,185 (R=pyrimidinyl and derivatives thereof); EP-A-324,347 (R=pyridazinyl and derivatives thereof); EP-A-300,278 (R=pyrrolyl or derivatives thereof); and U.S. Pat. No. 5,013,749 (R=imidazolyl and derivatives thereof).

Compounds suitable as active ingredients in the compositions are those, wherein R is selected from indolyl, pyrimidinyl, indenyl, pyrazolyl, pyrrolyl, imidazolyl, indolizinyl, pyrrolopyridine, pyrazolopyridine, quinolinyl, phenylsilylphenyl, naphthyl, cyclohexyl, phenylthienyl, phenylfuryl and pyridazinyl radical and derivatives thereof. Preferred are those compounds of formula I wherein R is selected from indolyl, pyrimidinyl, indenyl, quinolinyl and pyridinyl radicals and derivatives thereof and X is (E)—CH=CH—.

Specific examples of compounds disclosed in the above or other publications, which are HMG-CoA reductase compounds suitable to be employed as the drug active agent in the compositions of the invention, comprise the following sodium salts, or other pharmaceutically acceptable salts:

erythro-3R,5S-(E)-7-[4-(4-fluorophenyl)-6-(1-methylethyl)-2-dimethylamino-pyrimidin-5-yl]-3,5-dihydroxy-6-heptenoic acid, sodium salt;

erythro-(±)-(E)-7-[3-(4-fluorophenyl)-spiro[cyclopentane-1,1′-1H-inden]-2′-yl]-3,5-dihydroxy-6-heptenoic acid, sodium salt;

erythro-3R,5S-(E)-7-[3-(4-fluorophenyl)-1-(1-methylethyl)-indolizin-2-yl]-3,5-dihydroxy-6-heptenoic acid, sodium salt;

erythro-3R,5S-(E)-7-[3-(4-fluorophenyl)-1-(1-methylethyl)-1H-pyrrolo[2,3-b]pyridin-2-yl]-3,5-dihydroxy-6-heptenoic acid, sodium salt;

erythro-3R,5S-(E)-7-[4-(4-fluorophenyl)-2-(1-methylethyl)-quinolin-3-yl]-3,5-dihydroxy-6-heptenoic acid, sodium salt;

erythro-3R,5S-(E)-7-[1-(4-fluorophenyl)-3-(1-methylethyl)-4-oxo-1,4-dihydro-quinolin-2-yl]-3,5-dihydroxy-6-heptenoic acid, sodium salt;

erythro-3R,5S-(E)-7-[4-(4-fluorophenyl)-6-(1-methylethyl)-3-methyl-1H-pyrazolo[3,4-b]pyridin-5-yl]-3,5-dihydroxy-6-heptenoic acid, sodium salt;

erythro-3R,5S-(E)-7-[3-(1-methylethyl)-5,6-diphenyl-pyridazin-4-yl]-3,5-dihydroxy-6-heptenoic acid, sodium salt;

erythro-3R,5S-(E)-7-[4-(4-fluorophenyl)-6-(1-methylethyl)-2-phenylpyrimidin-5-yl]-3,5-dihydroxy-6-heptenoic acid, sodium salt;

erythro-3R,5S-(E)-7-[4-(4-fluorophenyl)-1-(1-methylethyl)-3-phenyl-2-oxo-2,3-dihydroimidazol-5-yl]-3,5-dihydroxy-6-heptenoic acid, sodium salt;

erythro-3R,5S-(E)-7-[4-(4-fluorophenyl)-2-(1-methylethyl)-1-oxo-1,2-dihydro-quinolin-3-yl]-3,5-dihydroxy-6-heptenoic acid, sodium salt;

erythro-(±)-(E)-7-[4-(4-fluorophenyl)-2-(1-methylethyl)-quinolin-3-yl]-3,5-dihydroxy-6-heptenoic acid, sodium salt;

erythro-(±)-(E)-7-[1-(4-fluorophenyl)-3-(1-methylethyl)-pyrrolo[2,1-a]isoquinolin-2-yl]-3,5-dihydroxy-6-heptenoic acid sodium salt;

erythro-(±)-(E)-7-[4-cyclopropyl-6-(4-fluorophenyl)-2-(4-methoxyphenyl)-pyrimidin-5-yl]-3,5-dihydroxy-6-heptenoic acid, sodium salt;

erythro-3R,5S-(E)-7-[4-(4-fluorophenyl)-2,6-dimethylpyrimidin-5-yl]-3,5-dihydroxy-6-heptenoic acid, sodium salt;

erythro-3R,5S-(E)-7-[4-(4-fluorophenyl)-6-methyl-2-phenyl-pyrimidin-5-yl]-3,5-dihydroxy-6-heptenoic acid, sodium salt;

erythro-3R,5S-(E)-7-[4-(3,5-dimethylphenyl)-6-methyl-2-phenyl-pyrimidin-5-yl]-3,5-dihydroxy-6-heptenoic acid, sodium salt;

erythro-(±)-(E)-7-[3,4-bis(4-fluorophenyl)-6-(1-methylethyl)-pyridazin-5-yl]-3,5-dihydroxy-6-heptenoic acid, sodium salt;

erythro-(±)-(E)-7-[1-(4-fluorophenyl)-3-(1-methylethyl)-5-phenyl-1H-pyrrol-2-yl]-3,5-dihydroxy-6-heptenoic acid, sodium salt;

erythro-(±)-(E)-9,9-bis(4-fluorophenyl)-3,5-dihydroxy-8-(1-methyl-1H-tetrazol-5-yl)-6,8-nonadienoic acid, sodium salt;

erythro-(±)-(E)-3,5-dihydroxy-9,9-diphenyl-6,8-nonadienoic acid, sodium salt;

erythro-(±)-(E)-7-[4-(4-fluorophenyl)-1,2-bis(1-methylethyl)-3-phenyl-pyrrol-2-yl]-3,5-dihydroxy-6-heptenoic acid, sodium salt;

erythro-3R,5S-(E)-7-[4,5-bis(4-fluorophenyl)-2-(1-methylethyl)-1H-imidazol-1-yl]-3,5-dihydroxy-6-heptenoic acid, sodium salt;

erythro-3R,5S-(E)-7-[4-(4-fluorophenyl)-2,6-bis(1-methylethyl)-5-methoxymethyl-pyridin-3-yl]-3,5-dihydroxy-6-heptenoic acid, sodium salt;

erythro-(±)-(E)-[4-(4-fluorophenyl)-2-(1-methylethyl)-6-phenyl-pyridin-3-yl]-3,5-dihydroxy-6-heptenoic acid, sodium salt;

erythro-(±)-(E)-[2-(4-fluorophenyl)-4,4,6,6-tetramethyl-cyclohexen-1-yl]-3,5-dihydroxy-6-heptenoic acid, sodium salt;

erythro-(±)-(E)-7-[4-(4-fluorophenyl)-2-(1-methylethyl)-quinolin-3-yl]-3,5-dihydroxy-6-heptenoic acid, sodium salt;

erythro-(±)-(E)-7-[4-(4-fluorophenyl)-2-cyclopropyl-quinolin-3-yl]-3,5-dihydroxy-6-heptenoic acid, sodium salt;

The compounds of formula I are HMG-CoA reductase inhibitors, i.e., cholesterol biosynthesis inhibitors, and, therefore, they are useful for the treatment of hyperlipoproteinemia and atherosclerosis as disclosed in the aforementioned patents, published applications and publications which have been incorporated by reference.

The following Examples are intended to illustrate the invention in various of its embodiments without being limitative in any way thereof.

EXAMPLE 1

A 20 mg No. 3 size oral fluvastatin capsule is prepared comprising the following formulation:

TABLE 1

| Ingredient | Amount (mg) |
| --- | --- |
| fluvastatin | 21.06 |
| calcium carbonate, USP[a] | 62.84 |
| sodium bicarbonate, USP | 2.00 |
| microcrystalline cellulose, NF[b] | 23.35 |
| pregelatinized starch, NF[c] | 20.95 |
| purified water, USP | q.s.* |
| set-asides: | |
| microcrystalline cellulose | 33.88 |
| pregelatinized starch | 20.95 |
| talc, USP | 9.43 |

TABLE 1-continued

| Ingredient | Amount (mg) |
|---|---|
| magnesium stearate, NF | 1.05 |

[a] heavy, precipitated
[b] Avicel, PH 102, FMC Corp.
[c] Starch 1500, Colorcon Corp.
*removed during processing (a) The fluvastatin, 2 mg sodium bicarbonate, 62.84 mg calcium carbonate, 23.35 mg microcrystalline cellulose, and 20.95 mg pregelatinized starch, are mixed for five minutes and the mixture is passed through a 40 mesh screen and blended for another three minutes.

(b) Water is added to the mixture, while blending for about four minutes, to form a wet granulation.

(c) The wet granulation is dried in a fluid bed dryer at 50° C. inlet temperature to an L.O.D. of 1.59%.

(d) The dried granules are passed through a 20 mesh screen and blended with the microcrystalline cellulose and pregelatinized starch set-asides for about ten minutes. Talc and magnesium stearate (each pre-screened on 60 mesh bolting cloth) are added to the mixture while blending for about 5 minutes.

The resulting composition has an L.O.D. of 2.65%.

A dispersion of the composition in 10–100 ml. of water has a pH of 10.

(e) A blue opaque capsule is filled with the composition and polished manually with salt.

The capsule meets a dissolution specification of 75% in 30 minutes by the USP paddle method.

The drug is found to be 99% intact after 18 months at 30° C. in a light protected, moisture-resistant environment.

EXAMPLE 2

In the same manner as described in Example 1, 40 mg double-sized No. 3 capsules are prepared employing twice the amounts of ingredients indicated in Table 1.

EXAMPLE 3

In the same manner as described in Example 1, 10 mg No. 3 fluvastatin capsules are prepared except that an additional 10 mg of microcrystalline cellulose is utilized.

EXAMPLE 4

A 20 mg oral fluvastatin tablet is prepared comprising the following formulation:

TABLE 2

| Ingredient | Amount (mg) |
|---|---|
| fluvastatin | 21.06 |
| calcium carbonate, USP | 25.00 |
| sodium bicarbonate, USP | 25.00 |
| microcrystalline cellulose, NF[d] | 118.94 |
| croscarmellose sodium, NF[e] | 3.00 |
| polyvinylpyrrolidone, USP[f] | 6.00 |
| magnesium stearate, NF | 1.00 |
| purified water, USP | q.s.* |

[d] Avicel PH 101 (FMC Corp.)
[e] Ac-Di-Sol (FMC Corp.)
[f] Kollidon 30 (BASF Corp.)
*removed during processing (a) The fluvastatin, calcium carbonate, sodium bicarbonate, microcrystalline cellulose, polyvinyl pyrrolidone, and croscarmellose sodium, are each passed through a 40 mesh screen, and then combined and mixed for 3 minutes, and the resulting mixture is passed through a 40 mesh screen, and mixing is continued for 2 minutes.

(b) Water is added to the resulting mixture, while blending for about 5 minutes to form a wet granulation.

(c) The granulation is dried in a fluid bed dryer with inlet temperature of 50° C. until L.O.D. of the granules is 6 to 8%. The granules are passed through a 14 mesh screen and redried until L.O.D. is not greater than 2.5%. The dried granules are passed through a 24 mesh screen, and blended for three minutes.

(d) Magnesium stearate, passed through a 60 mesh bolting cloth, is blended into the mixture for five minutes.

The resulting composition has an L.O.D. of not greater than 2%.

A dispersion of the composition in 10–100 ml of water has a pH of 10.

(e) The resulting light yellow colored composition is tableted using an 8 mm punch, to form a 200 mg tablet core.

(f) A hydroxypropylmethylcellulose film coating formulation, Opadry Yellow[T], YS-1-6347-G, Colorcon Corp. (10% aqueous suspension), is applied to the tablet core in a fluidized bed with an inlet temperature set at 70°–75° C., to result in a 5–6% tablet weight gain.

The resulting tablet meets a dissolution specification of 75% in 30 minutes by the USP paddle method.

The drug is found to be 99% intact after 18 months at 30° C. in a light protected, moisture-resistant environment.

EXAMPLE 5

In the same manner as described in Example 4, 40 mg fluvastatin tablets are prepared wherein the ingredients of the tablet core are present in twice the amounts indicated in Example 4.

EXAMPLE 6

In the same manner as described in Example 4, 10 mg fluvastatin tablets are prepared wherein the ingredients of the tablet core are present in half the amounts indicated in Example 4.

EXAMPLE 7

A fluvastatin tablet core or capsule prepared as described in any one of the above Examples is coated in a fluidized bed at a bed temperature of 30°–50° C., inlet temperature of 50°–80° C., and a relative humidity of less than 50% with an enteric coating formulation comprising Eudragit ® (Rohm Pharma) or, alternatively, hydroxypropylmethylcellulose phthalate, to result in a weight percent increase of about 5–12%.

EXAMPLE 8

A composition according to the invention is prepared as described in any one of the above Examples which comprises erythro-3R,5S-(E)-7-[4-(4-fluorophenyl)-6-(1-methylethyl)-2-dimethylamino-pyrimidin-5-yl]-3,5-dihydroxy-6-heptenoic acid, sodium salt, or its 3R,5S isomer, as the active agent.

EXAMPLE 9

A composition according to the invention is prepared as described in any one of the above Examples which comprises erythro-(±)-(E)-7-[3-(4-fluorophenyl)- spiro[cyclopentane-1,1'-1H-inden]-2'-yl]-3,5-dihydroxy-6-heptenoic acid, sodium salt, or its 3R,5s isomer, as the active agent.

EXAMPLE 10

A composition according to the invention is prepared as described in any one of the above Examples which comprises erythro-3R,5S-(E)-7-[4-(4-fluorophenyl)-2,6-bis(1-methylethyl)-5-methoxymethyl-pyridin3-yl]-3,5-dihydroxy-6-heptenoic acid, sodium salt, or its racemate, as the active agent.

EXAMPLE 11

A composition according to the invention is prepared as described in any one of the above Examples which comprises erythro-(±)-(E)-[4-(4-fluorophenyl)-2-(1-methylethyl)-6-phenyl-pyridin-3-yl]-3,5-dihydroxy-6-heptenoic acid, sodium salt, or its 3R,5S isomer, as the active agent.

EXAMPLE 12

A composition according to the invention is prepared as described in any one of the above Examples which comprises erythro-(±)-(E)-7-[4-(4-fluorophenyl)-2-(1-methylethyl)-quinolin-3-yl]-3,5-dihydroxy-6-heptenoic acid, sodium salt, or its 3R,5S isomer, as the active agent.

EXAMPLE 13

A composition according to the invention is prepared as described in any one of the above Examples which comprises erythro-(±)-(E)-7-[4-(4-fluorophenyl)-2-cyclopropyl-quinolin-3-yl]-3,5-dihydroxy-6-heptenoic acid, sodium salt, or its 3R,5S isomer, as the active agent.

What is claimed is:

1. A pharmaceutical composition comprising an HMG-CoA reductase inhibitor compound of the formula:

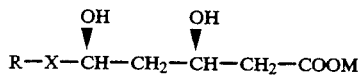

wherein
R is an organic radical,
X is —CH=CH—, and
M is a physiologically acceptable cation,
and an alkaline stabilizing medium capable of imparting a pH of at least 8 to an aqueous solution or dispersion of the composition wherein the alkaline stabilizing medium comprises at least one pharmaceutically acceptable carbonate salt.

2. A pharmaceutical composition according to claim 1 wherein R is selected from the group consisting of indolyl, pyrimidinyl, indenyl, pyridinyl and quinolinyl radicals and derivatives thereof, and X is (E)—CH=CH—.

3. A pharmaceutical composition according to claims 2 wherein the pharmaceutically acceptable carbonate salt is selected from the group consisting of sodium carbonate, sodium bicarbonate, calcium carbonate and mixtures thereof.

4. A pharmaceutical composition according to claim 1 wherein the alkaline stabilizing medium comprises a mixture of a water soluble carbonate and a water insoluble or sparingly soluble carbonate.

5. A pharmaceutical composition according to claim 4 wherein the ratio of water soluble carbonate to water insoluble or sparingly soluble carbonate is from 1:40 to 2:1.

6. A pharmaceutical composition comprising the HMG-CoA reductase inhibitor fluvastatin sodium and a pharmaceutically acceptable alkaline stabilizing medium capable of imparting a pH of at least 8 to an aqueous solution or dispersion of the composition.

7. A pharmaceutical composition according to claim 6 wherein the alkaline stabilizing medium comprises at least one pharmaceutically acceptable carbonate salt.

8. A pharmaceutical composition according to claim 7 wherein the pharmaceutically acceptable carbonate salt is selected from the group consisting of sodium carbonate, sodium bicarbonate, calcium carbonate and mixtures thereof.

9. A pharmaceutical composition according to claim 8 comprising fluvastatin sodium, (i) calcium carbonate and (ii) sodium carbonate or sodium bicarbonate.

10. A pharmaceutical composition according to claims 1, 3, or 8 which comprises 0.5 to 60 wt. % HMG-CoA reductase inhibitor compound, 0.5 to 40 wt. % calcium carbonate, 0.5 to 20 wt. % sodium bicarbonate, and 10 to 65 wt. % microcrystalline cellulose.

11. A pharmaceutical composition according to claims 2 or 6 in solid unit dosage form.

12. An oral pharmaceutical composition suitable for excapsulation for delivering fluvastatin sodium which comprises 0.5 to 60 wt. % of fluvastatin sodium,
25 to 40 wt. % of calcium carbonate,
0.5 to 10 wt. % of sodium bicarbonate, and
20 to 35 wt. % of microcrystalline cellulose.

13. An oral pharmaceutical composition suitable for tableting for delivering fluvastatin sodium which comprises
0.5 to 60 wt. % of fluvastatin sodium,
5 to 20 wt. % of calcium carbonate,
5 to 20 wt. % of sodium bicarbonate, and
50 to 65 wt. % of microcrystalline cellulose.

14. A composition according to claim 12 wherein the capsule is coated with an enteric and/or film coating.

15. A composition according to claim 13 wherein the tablet is coated with an enteric and/or film coating.

16. A composition according to claim 12 wherein fluvastatin sodium is present in a dosage amount selected from the group consisting of 5, 10, 15, 20 and 40 mg. amounts.

17. A composition according to claim 13 wherein fluvastatin sodium is present in a dosage amount selected from the group consisting of 5, 10, 15, 20 and 40 mg. amounts.

18. A composition according to claims 2 or 8 wherein the HMG-CoA reductase inhibitor compound and the pharmaceutically acceptable carbonate salt are in intimate contacting association.

19. A method of preparing the composition of claims 2 or 8 which comprises bringing the HMG-CoA reductase inhibitor compound and the alkaline stabilizing medium into intimate contacting association by co-lyophilizing the HMG-CoA reductase inhibitor compound and the alkaline stabilizing medium.

20. A pharmaceutical composition according to claim 2 wherein the HMG-CoA reductase inhibitor compound is a pharmaceutically acceptable salt of erythro-3R,5S-(E)-7-[4-fluorophenyl-6-(1-methylethyl)-2-(dimethylamino-pyrimidin-5-yl)-3,5-dihydroxy-6-heptenoic acid, or its racemate.

21. A pharmaceutical composition according to claim 2 wherein the HMG-CoA reductase inhibitor compound is a pharmaceutically acceptable salt of erythro-3R,5S-(E)-dimethoxy-7-[3'-(4''-fluorophenyl)-spiro[cyclopentane-1,1'(1H)-inden]-2'-yl]-3-hydroxyhept-6-enoic acid, or racemate.

22. A pharmaceutical composition according to claim 2 wherein the HMG-CoA reductase inhibitor compound is a pharmaceutically acceptable salt of erythro-3R,5S-(E)-7-[4-(4-fluorophenyl)-2,6-bis(1-methylethyl)-5-methoxymethyl-pyridin-3-yl]-3,5-dihydroxy-6-heptenoic acid, or its racemate.

23. A pharmaceutical composition according to claim 2 wherein the HMG-CoA reductase inhibitor compound is a pharmaceutically acceptable salt of erythro-(±)-(E)-[4-(4-fluorophenyl)-2-(1-methylethyl)-6-phenyl-pyridin-3-yl]-3,5- dihydroxy-6-heptenoic acid, or its 3R,5S isomer.

24. A pharmaceutical composition according to claim 2 wherein the HMG-CoA reductase inhibitor compound is a pharmaceutically acceptable salt of erythro-(±)-(E)-7-[4-(4-fluorophenyl)-2-(1-methylethyl)-quinolin-3-yl]-3,5-dihydroxy-6- heptenoic acid, or its 3R,5S isomer.

25. A pharmaceutical composition according to claim 2 wherein the HMG-CoA reductase inhibitor compound is a pharmaceutically acceptable salt of erythro-(±)-(E)-7-[4-(4-fluorophenyl)-2-cyclopropyl-quinolin-3-yl]-3,5-dihydroxy-6-heptenoic acid, or its 3R, 5S isomer.

26. A pharmaceutical composition according to claim 2 which comprises erythro-(E)-3R,5S-7-[3-(4-fluorophenyl)-1-(1-methylethyl)-1H-indol-2-yl]-3,5-dihydroxy-6-heptenoic acid, sodium salt.

27. A pharmaceutical composition according to claims 2 or 7 which comprises 0.5 to 60 wt. % HMG-CoA reductase compound, 10 to 55 wt. % pharmaceutically acceptable carbonate salts, and 10 to 65 wt. % filler.

* * * * *